United States Patent [19]

Skov et al.

[11] Patent Number: 5,041,390

[45] Date of Patent: Aug. 20, 1991

[54] METHOD AND MEANS FOR ALLERGY DIAGNOSIS

[76] Inventors: Per S. Skov, Kanslergade 6, st.th., DK-2100 Copenhagen O; Ole-Christian Bjarno, Pilekaeret 26, DK-2840 Holte, both of Denmark

[21] Appl. No.: 258,528

[22] Filed: Oct. 17, 1988

[30] Foreign Application Priority Data

Aug. 11, 1988 [DK] Denmark .............................. 4510/88
Aug. 12, 1988 [DK] Denmark .............................. 4551/88

[51] Int. Cl.$^5$ .......................................... G01N 33/552
[52] U.S. Cl. .................................... 436/527; 436/541; 436/804; 435/29
[58] Field of Search ............... 436/527, 541, 804; 435/29

[56] References Cited

U.S. PATENT DOCUMENTS 4,550,085 10/1985 Skov et al. ............................ 436/98

OTHER PUBLICATIONS

Merck Index 10th Edition, p. 1395, 1983.

*Primary Examiner*—Christine Nucker
*Assistant Examiner*—Jeffrey Stucker
*Attorney, Agent, or Firm*—Darby & Darby

[57] ABSTRACT

The histamine in a sample is determined by contacting the sample with a histamine binding agent, such as glass, which has been treated, e.g., with a polar organic polymer, to reduce the affinity of the agent for an interfering component of the sample while substantially retaining the agent's histamine binding capacity. Such an agent facilitates determination of histamine in whole blood samples. Preferably, the agent is provided as a conglomerate of histamine-binding bodies, such as glass fibers, in a binder. Preferred binders are polyvinyl acetate, a vinyl acetate/ethylene copolymer, and polyvinyl alcohol or combinations thereof.

35 Claims, 3 Drawing Sheets

METHOD AND MEANS FOR ALLERGY DIAGNOSIS

BACKGROUND OF THE INVENTION

Field of the Invention

The present invention provides a method and a test set for determining histamine present in samples, in particular whole blood, obtained from allergic patients. The method is based on a selective binding of histamine to certain materials, and is useful in the diagnosis of allergy related to specific allergens.

Information Disclosure Statement

It is essential for allergic patients to know which of the allergens present in their environment or diet give rise to the allergic reaction. Thus, there is a pressing need for the development of accurate, precise, easily applicable and inexpensive methods for establishing which allergens are relevant for the patient.

Methods based on imitation of the in vivo reaction involve the following:

It is known that allergenicity may be evaluated by exposing certain cells, obtained from the patient, to the allergens considered to be of importance, thus inducing a histamine release from said cells, and subsequent measuring the amount of histamine released.

A method based on this principle is described in U.S. Pat. No. 4,550,085. In the latter method, the cell phase contacted with the allergens in question was a specially prepared cell suspension, namely a cell suspension enriched with leucocytes. To prepare this suspension, blood was drawn from the patient, and the erythrocytes were sedimented. The leucocyte-enriched plasma layer obtained was carefully transferred to another container, suspended in a buffer, and then centrifuged in order to isolate the leucocytes from the major part of the plasma. The supernatant obtained was removed, and the pelleted leucocytes were resuspended in a buffer. This step was further repeated to yield a cell suspension especially enriched with basophile leucocytes.

Accordingly, the sample applied directly to the glass fiber coated assay tray was not whole blood as such, but a blood sample which had been subjected to several intermediate treatments.

SUMMARY OF THE INVENTION

The present invention provides a method for the determination of histamine released by the leucocytes of whole blood, said method permitting direct employment of whole blood without the need for initial isolation/washing steps. For several reasons, it is clearly advantageous to be able to employ whole blood directly, i.e. to contact the blood directly with a compartment containing a histamine release-inducing agent and histamine-binding material;

the omission of various fractionation steps results in increased accuracy and precision of the assay;

time-consuming blood fractionation is avoided and hence the total analysis time is significantly reduced;

the requirement for centrifugation equipment is eliminated;

the risk of contaminating the sample material during fractionation steps is eliminated;

the risk of inducing artificial changes in the histamine release ability of the cells during centrifugation and washing manipulations is eliminated;

the risk of operator contact with any pathogenic agents, such as infectious and/or toxic agents, present in the blood sample is minimized;

the risk of mistaken exchange of samples from different patients is reduced;

the amount of blood necessary for the analysis is reduced.

Despite these reasons for analyzing whole blood samples, allergenicity is presently analyzed using specially processed leukocyte samples. The justification is that whole blood contains various components, notably hemoglobin, which interfere with a histamine-binding assay. The present inventors have overcome this problem by contacting the sample with a histamine-binding inorganic material which has been treated to reduce the polarity and/or surface tension of its surface so that its affinity for an interfering component, such as hemoglobin, has been reduced while its histamine-binding capacity has been substantially retained.

After incubation of the sample with the histamine-binding material, the two are separated and the latter is preferably washed with agents that remove interfering components without seriously affecting the bound histamine. When the histamine-binding material is available in the form of granules, flakes, fibers, etc., it is preferable to conglomerate these discrete bodies using a suitable binder, as the resulting conglomerate will better survive the rigors of the washing step. Thus, in another preferred embodiment, such a conglomerate is used as the histamine binding agent in the contemplated assay. Preferably, the binder also reduces the polarity and/or the surface tension of the histamine binding material.

Further aspects of the invention are set forth in the following description and claims.

BRIEF DESCRIPTION OF THE DRAWINGS

FIG. 1 shows a diagrammatic view of a test set according to the invention in the form of a tray comprising wells with histamine-binding glass fibres therein.

DETAILED DESCRIPTION OF THE INVENTION

The present invention is particularly related to determining histamine in samples obtained from humans or animals. Especially, the invention relates to the determination of histamine in body fluids. Important examples of body fluids are blood and various other fluids which contain histamine-containing cells and/or cells which release histamine.

Such fluids and other body fluids often contain hemoglobin or hemoglobin-like components, or globin-containing components, or other components which have a tendency to adhere to histamine-binding material, and/or to interfere with the effective binding of histamine to histamine-binding material. These interfering components may either be present in the fluid phase or in cells present in the body fluid samples. In cases where such biological components have a high affinity to the histamine-binding material, in particular histamine-binding inorganic materials, they may tend to build up a phase or physical-chemical barrier which would prevent histamine from properly binding with a histamine-binding material—and/or these components may compete with histamine in the binding to histamine-binding material. Therefore, it is important to employ agents and methods which will counteract the interference from such components. The present invention provides such solutions.

Especially relevant is a modification of the histamine-binding material which modifies the surface of the material in such a manner that binding of biological components other than histamine, otherwise showing a strong adhesion to the surface, is reduced without unduly impairing histamine binding.

The term "whole blood or substantially whole blood" is often used. The term "substantially whole blood" is intended to designate blood samples which retain all of or a considerable proportion of the erythrocytes originally present in blood samples from a patient. Whole blood may either be whole blood as drawn from the patient, or such whole blood which has been slightly modified such as by dilution, as distinct from treatments such as fractionation by centrifugation or other labour-consuming blood fractionation procedures.

Blood may be taken by venipuncture by from an individual suspected of being allergic and collected into suitable containers, e.g. plastic or glass tubes (e.g. "Venoject" tubes). A suitable anticoagulant is preferably present in the container prior to the collection of blood. The anticoagulant is preferably an anticoagulant substantially not interfering with histamine release from the cells in question, e.g. not interfering with components essential to the reactions involved in the release or in the analysis procedure. Heparin, e.g. in the form of sodium or potassium heparinate, is a preferred anticoagulant. Typically 0.5 ml of a 30 U heparin/ml solution is employed so as to obtain 3 U heparin per ml blood when 5 ml blood was collected. Usually 5 ml blood is collected, however 2-3 ml provide enough sample material for testing for allergy to several allergens, e.g. 2.5 ml is used in a tray comprising 96 wells. For testing for allergy to a single allergen, as little as 1 ml of blood is sufficient.

In the present context the term "inorganic histamine-binding material" designates any material which is capable of binding histamine and which is of either inorganic character or predominantly inorganic character. Examples of such inorganic materials are described in greater detail below, including laboratory-prepared glass types which may contain minor proportions of organic residues but which are in the present context considered inorganic materials.

The term "determination" as used in the present context is normally used to denote measurement of concentration, but in certain instances is used to denote qualitative identification.

The determination may be performed by any suitable determination method having the necessary sensitivity, such as competitive determination, e.g. involving the use of labeled histamine, or direct determination, e.g. by spectrophotometry.

An example of a procedure for determination of histamine which is employed in a preferred embodiment of a method according to the present invention as exemplified herein is a fluorometric assay procedure. This procedure is based on coupling of histamine with a fluorophore, viz. ortho-phthaldialdehyde, with essentially quantitative formation of a fluorescent ring structure whose concentration can be related to measured fluorescence intensity. The underlying principle of this assay is described in Hoppe-Seyler's Z. Physiol. Chem. 353, 911-920, 1972.

In a preferred embodiment described herein, histamine is freed from the the histamine-binding material at high pH ($>10$), the high pH also being required for satisfactory reaction between freed histamine and ortho-phthaldialdehyde (OPT). Perchloric acid is then added to reduce pH to a low value necessary for ensuring adequate stability of the fluorescent reaction product formed between histamine and OPT.

By the term "conglomerate" is meant any physical composite of the histamine-binding material and the binder. The histamine-binding material may be in the form of a body or bodies of relatively macroscopic dimensions; it may also be of more microscopic dimensions, suitably in the form of fibers. Fibers in the present context normally have a length:diameter ratio of at least 4:1.

When the bodies of histamine-binding material are in the form of fibers, such fibers are advantageously employed in the form of microfibers, for example microfibers formed by comminution of longer fibers. The length of such microfibers is preferably between 0.5 and 100 (or even 200) m, more preferably from 1 to 50 m, especially from 1 to 25 m, in particular 2 to 20 m: the diameter is preferably between 0.1 and 10 m, more preferably 0.2 to 5 m, in particular 0.3 to 2 m.

The conglomerate may thus comprise fragments of histamine-binding material, for example flakes, pieces of sheet, or lumps of dimensions greater than or equal to several millimeters, wholly or partly covered with the binder. At the other extreme, the conglomerate may comprise microscopic bodies of histamine-binding material of dimensions such as those mentioned above for microfibers, these microscopic bodies being gathered into a mass or coherent whole which is bound together by the binder. This mass or coherent whole may, for example, take the form of roughly spherical or more irregularly shaped entities, the individual microscopic bodies of which may or may not be wholly or partially covered by the binder. It may also, as in a preferred embodiment of the present invention, adopt a form dictated by the geometry of a carrier to which the conglomerate is affixed. In the preferred embodiment of the invention, the carrier is the bottom of a well in a polystyrene tray, the conglomerate adopting the form shown diagrammatically in FIG. 1 (vide infra).

The bodies of histamine-binding material may also be in the form of powder or other particles, including porous particles; they may further be, for example, porous and/or fibrous or otherwise subdivided (to obtain a high surface area) domains of otherwise substantially continuous bodies such as sheets (or, e.g., well sides and/or bottoms) which domains have been prepared, e.g., by casting, mechanical, thermal, electrical and/or chemical roughening treatment, e.g. etching, or other means suitable for providing domains with elements of a high surface area.

In the present context the term "carrier" designates any suitable support device to which the conglomerate may suitably be affixed, such as a container or vessel, or microcontainer or microvessel, a tube, or any other kind of solid support to which the conglomerate is suitably affixed for the purpose of the analysis.

It may, for example, be in the form of a micro-scale column comprising a filter capable of supporting the glass bodies, so that the glass bodies can be contacted with a histamine-containing sample and then eluted with relevant reagents or media.

However, also other kinds of carriers or supports are possible, such as bodies which in themselves are not capable of housing any liquid but which are designated for being immersed in a liquid for example beads such as solid or hollow beads, or entities of various shapes in small sizes designated for immersion into a sample.

The carrier preferably consists of a material which is substantially inert under the reaction conditions prevailing during determination, for example a thermoplastic synthetic resin such as polystyrene.

The inorganic histamine-binding material may be either substantially amorphous or substantially crystalline in structure, and may very suitably be silicon dioxide based material, that is, material containing a significant amount or a major proportion of silicon dioxide, or made from or formed from material comprising a significant amount or a major proportion of silicon dioxide. Such a material can, for example, be silicon dioxide based glass materials or quartz.

The term "glass material" as used in the present context denotes a material which is based wholly or partly upon silicon dioxide, and which has a substantially amorphous structure and an extremely high viscosity.

Examples of important types of glass which might be used in the present invention include:

silicon dioxide glass, consisting of amorphous, fused silicon dioxide;

soda-lime glass, consisting typically of a fused homogeneous mixture of silica (ca. 75%), soda ash (ca. 20%) and lime (ca. 5%).

borosilicate glass, which is normally a soda-lime type glass, further containing boric oxide (often ca. 5%). The glass material of Whatman GF/B glass fiber sheet (vide infra) is an example of a typical borosilicate glass.

A number of types of glass of the soda-lime type tailored to meet requirements for specific properties are also produced by the further incorporation of certain metallic oxides, for example oxides of magnesium, barium, lead, zinc, aluminium, lithium or cerium.

U.S. Pat. No. 4,550,085 discloses advantages associated with the use of glass microfibers prepared from glass microfiber filter sheet marketed under the name of Whatman GF/B for selectively binding histamine. According to the manufacturer's product information, the borosilicate glass from which these fibers are fashioned is a borosilicate glass of relatively high boric oxide content as can be seen in the following table (Table 1) specifying the typical composition of this glass:

|  | % (w/w) |
| --- | --- |
| $SiO_2$ | 57.9 |
| $B_2O_3$ | 10.7 |
| $Fe_2O_3$ | 5.9 |
| $Al_2O_3$ | 10.1 |
| $Na_2O + K_2O$ | 2.9 |
| CaO | 2.6 |
| MgO | 0.4 |

-continued

|  | % (w/w) |
| --- | --- |
| BaO | 5.0 |
| ZnO | 3.9 |
| F | 0.6 |

Selective histamine-binding at a level satisfactory for use in a method according to the present invention is not confined to glass of the borosilicate type in that, e.g. pure silicon dioxide glass, a number of laboratory-prepared glasses of composition similar to glass of the soda-lime type, but without calcium oxide as a component, and a number of laboratory-prepared glasses prepared partly on the basis of metal or non-metal alkoxides as components all appear to exhibit useful histamine-binding properties.

An example of a crystalline silicon dioxide based material is quartz, i.e. pure, crystalline $SiO_2$, which has been found by the present applicant to exhibit histamine-binding properties.

Based upon the disclosure of U.S. Pat. No. 4,550,085 and the present disclosure, the person skilled in the art will be able to determine the histamine-binding properties of other types of materials not specifically mentioned here.

In view of the ready commercial availability and reproducibility of Whatman GF/B glass microfibers, however, these microfibers are presently preferred as starting material for the preparation of glass microfiber for use in a method according to the invention, an example of a preferred embodiment of the preparation of such glass microfibers from Whatman GF/B glass fiber filter sheet being described in detail in Example 1 (vide infra).

In the present context, the term "binder" is intended to designate any substances that is capable of bonding other substances together by surface attachment. Naturally, the binders used according to the present invention should be binders which result in a suitable conglomeration of the histamine-binding bodies while at the same time leaving sufficient access of histamine-containing fluids to the bodies. From a chemical point of view, the binders should be so selected that they do not adversely influence the measured results. The binders may suitably be binders which are synthetic organic polymers and, as they are to bind and retain the conglomerate in situ during contact with normally water-containing samples, it is preferred that the polymers are substantially water-insoluble although binders which are applied from e.g. an aqueous dispersion are perfectly suitable for the purpose of the present invention provided that they will remain substantially water-insoluble once they have been applied.

As examples of suitable binders may be mentioned polyvinyl esters such as polyvinylacetate or copolymers such as vinyl acetate/ethylene copolymers, optionally in combination with polyvinyl alcohol. As will appear from the following explanation, the latter type of binders may, together with their binding capacity, show surprising advantages with respect to reducing interference from body fluid components such as hemoglobin in the sample.

The amount of binder to be applied will depend upon the character of the binder and the histamine-binding bodies. It is believed that suitable ranges of binders are from about 0.8 to about 10 percent solid weight, in particular from about 2 to about 6 percent solid weight of binder, calculated on the basis of the histamine-binding material.

According to a particular and important aspect of the invention, the histamine-binding material is an inorganic material which has been treated to reduce the polarity and/or surface tension of its surface so that its adhesive forces (affinity) towards interfering components in the samples examined, in particular samples of body fluids (especially samples of whole blood or substantially whole blood or other body fluid samples in which erythrocytes or erythrocyte components/fractions or components of similar interfering character, in particular hemoglobin or hemoglobin fragments or hemoglobin-like components are present in significant amounts), have been reduced while the histamine-binding capacity of the glass has been substantially retained.

As will be understood, an inorganic material, of which the adhesive forces towards hemoglobin have been reduced will also normally show substantially reduced adhesive forces towards other interfering components in body fluid samples (because hemoglobin can, in many contexts of relevance herein, be considered representative of the interfering substances) and will thus show distinct advantages in the method of the invention.

Therefore, a measure of the usefulness of the treatment of an inorganic material to reduce its adhesive forces towards interfering substances may normally be obtained by ascertaining the behaviour of the treated material towards hemoglobin or a hemoglobin analogue or another related globin such as, e.g., myoglobin; a reduction of the adhesive forces towards hemoglobin or hemoglobin analogues or other related globins with retainment of adequate histamine binding is thus an indication of increased utility of a treated inorganic histamine-binding material for the general purposes of the present invention.

While the term "treatment" is used in the present context, it will be understood that the reduced polarity of the surface of an inorganic histamine-binding material may also be obtained by incorporation of polarity-reducing or surface tension-reducing substances during the production of the inorganic material; in the present specification and claims, this possibility is included in the term "treated" or "treatment", or "prepared."

A reduction of the polarity and/or surface tension of the surface of a histamine-binding inorganic material (glass being used as an example thereof in the following explanation) may be obtained by treatment with a polar organic polymer or a mixture of polar organic polymers. By this treatment, the glass surface is modified in a direction towards lower polarity with the effect that it has lower attraction or adhesive forces towards hemoglobin and other proteinaceous macromolecules and other components of the blood or biological fluid where a polar attraction otherwise would tend to bind these compounds to the glass. The work required to separate reversibly the interface between two phases can be expressed in the following equation:

$$gamma = gamma_A + gamma_B - gamma_{AB}$$

wherein $gamma_A$ is the surface tension of phase A, $gamma_B$ is the surface tension of phase B, and $gamma_{AB}$ is the interfacial tension between the two phases.

Thus, e.g. if A is a glass surface and B is for example a hemoglobin molecule, the $gamma_A$ and $gamma_B$ will both have a high value, whereas $gamma_{AB}$ will have a relatively low value, thus resulting in a high work of adhesion, gamma. By modifying the glass surface, so that we have a modified glass surface, $gamma_A$ will be lower, $gamma_B$ will retain its value, and $gamma_{AB}$ may be the same or higher, thus resulting in a lower work of adhesion.

By utilizing this principle, the binding of a highly adhesive blood macromolecule such as hemoglobin is reduced relative to the binding of histamine. With respect to histamine binding to the modified glass, the sum of the surface tension contributions for the modified glass surface and the histamine may well be lower than in the case of the non-modified glass, but on the other hand, the interfacial tension $gamma_{AB}$ will be lower so that the resulting work of adhesion gamma may well be substantially equal to that for the untreated glass.

Thus, the treatment of the surface of the inorganic histamine-binding material for the purpose of the present invention may be obtained by means of any agent which will result in a suitable reduction of the polarity or surface tension of the surface of the material, but with retention of the capability of the glass to bind histamine to an extent adequate for the determination.

Agents useful for this purpose are, for example, polar polymers, that are close to the polar histamine molecule with respect to solubility parameters, thereby exhibiting a non-barrier effect with respect to histamine's access to the histamine-binding surface, i.e. in particular polymers containing heteroatoms such as oxygen or nitrogen, examples of such groups being hydroxy groups, carboxy groups, ester groups, amino groups, imino groups, amide groups, carbonyl groups, ether groups, heterocyclic groups with heteroatoms such as oxygen or nitrogen.

Without specifying wide limits for suitable polymers, it should be mentioned that the polymer should not have such a high molecular weight that it cannot be distributed adequately over the glass surface.

The polymer may be applied in any suitable manner from a liquid dispersion or solution or it may be polymerized in situ from monomers.

The polymers are not limited to homopolymers but may suitably and in certain cases advantageously be copolymers or mixtures of polymers or mixtures of polymers and copolymers. The decisive feature is in all cases that the polymer is capable of conferring a decreased polarity to the glass surface while retaining the essential adequate histamine binding capacity.

The suitability of a polymer or copolymer or mixture of polymers and/or copolymers for the purpose of the invention may be determined by preliminary tests performed in accordance with known methods, such as contact angle measurements and tests of solubility parameters. The practical test in most cases is that the resulting treated glass surface should have, compared to the untreated glass surface, a reduced affinity to hemoglobin molecules and other potentially interfering sample components while retaining a useful histamine binding capacity.

The solubility parameters employed may suitably be those described in "Handbook of Solubility Parameters and other Cohesion Parameters," A. F. M. Barton, CRC Press (1983) (denoted hereafter ref. A), incorporated by reference herein, as pertinent. A useful model is the three-dimensional solubility parameter theory developed by Charles M. Hansen, which is useful for predicting the capability of solvents or solvent mixtures to dissolve polymers. The three solubility parameters employed in this model are the so-called "dispersion," "polar," and "hydrogen-bonding" parameters.

The solubility parameters for histamine may be calculated using a group-contribution method as described in ref. A., chapter 6.8, or may be determined empirically. The solubility parameters for the binder can likewise be determined by group-contribution methods (see ref. A, chapter 14.5), or empirically, or from data compilations (see e.g., ref. A, chapter 14.3). In the present context, this implies that the solubility parameters of the binder should be close to those of the histamine.

The solubility coordinates of histamine in Hansen's three-dimensional coordinate system lie within the solubility parameter sphere of the binder. If the histamine solubility parameter position is not encompassed by the solubility parameter sphere of the binder, the binder will act as a barrier for histamine, thus preventing access of histamine to the histamine-binding material. Preferably, histamine is freely soluble in the binder.

Apart from exhibiting the properties described above, preferred binders as used according to the present invention should also exhibit surface tension low enough to substantially prevent adhesion of interfering sample components, such as hemoglobin or other biological macromolecules. Relevant surface tension data can be found e.g., in "Polymer Interface and Adhesion," S. Wu, Marcel Dekker, New York and Basel (1982), incorporated by reference herein, as pertinent.

An aqueous suspension or dispersion of a vinyl acetate/ethylene copolymer stabilized with polyvinyl alcohol has been found to be an excellent polymer for the treatment of the glass surface to and has been found to simultaneously be capable of fixing the glass fibers to each other and to the support in accordance with another of the aspects of the invention. Therefore, the use of such a suspension or dispersion is presently preferred and is illustrated in examples hereinafter.

When the above-described Hansen theory is applied to the preferred histamine/binder combination according to the present invention, the theory does indeed predict that the solubility parameter position of histamine in the three-dimensional coordinate system is encompassed by the solubility parameter sphere of a vinylacetate-based copolymer of the type used, in other words that histamine should be able to migrate freely through a layer of such a binder deposited on a histamine-binding material. Preferably, the histamine-binding material is treated with an agent whose solubility parameter sphere encompasses the solubility parameter position of histamine.

The amount of polymer to be used in the treatment should be adapted to the particular inorganic material and the particular polymer used. In the cases where the same polymer or mixture of polymers is used to obtain both the surface-modifying effect and the binder effect, the amount will normally be higher than where surface modification is the only aim. However, there may be a gradual transition from a condition where a slight extent of surface modification has been obtained to a condition where a conglomerate of inorganic histamine-binding material has received such an amount of polymer that a major reason for the reduction of the interference by non-histamine components of the sample maybe more related to modified spatial/steric conditions at or in the vicinity of the histamine-binding surfaces.

A preferred embodiment of the present invention in which glass microfibers are fixed in tray wells with the aid of a binder provides the advantage that the fibres are mechanically fixed to the wells and able to withstand the washing procedures necessary for the removal of the undesired blood components.

In a further aspect of the present invention, a method for the determination of histamine in a sample of whole blood may further comprise the provision of an agent capable of inducing histamine-release from cells sensitive to the agent such that said agent is present together with the conglomerate so that the sample is contacted with both the agent and the conglomerate. Such an agent may be an allergen, i.e. an antigen which gives rise to an allergic reaction in certain individuals. Examples of important and relevant allergens are allergens which normally are airborne and can therefore be inhaled, such as allergens in pollen of birch, grass and mugwort, allergens in horse, dog or cat dander, dust, mite allergens and mould fungus allergens. Allergens which can be present in foods and beverages, and may therefore be ingested, include allergens of cow milk, chicken egg, rye flour, wheat flour, oat meal, pork, beef, codfish, soyabean, and green pea.

An important agent capable of inducing histamine-release from cells is anti-IgE.

It is clearly advantageous to incorporate an allergen in the same compartment as a conglomerate, since the user of the test-set is then freed from the necessity of acquiring and adding allergen extracts as well as adding the blood sample.

From the point of view of the shelf-life and handling, it is particularly advantageous to provide allergens in a substantially dry condition together with conglomerates. In a preferred embodiment of a test-set according to the present invention (vide infra) a carrier in the form of a well in a Microtiter tray incorporates dried standardized allergen extracts together with the conglomerate.

In a still further aspect of the present invention, a method for the determination of histamine in a sample of whole blood wherein an agent capable of inducing histamine-release from cells sensitive to the agent is present together with the conglomerate may further comprise the provision of an agent capable of enhancing the release of histamine from cells sensitive to the histamine release-inducing agent, such that the histamine release-enhancing agent is present together with the conglomerate and the histamine release-inducing agent. An example of such a histamine release-enhancing agent is histamine itself. Histamine included for the purpose of enhancing histamine release from cells should be included in an amount which is effective to obtain the enhancement, but which is not toxic to the cells and is preferably included in an amount corresponding to a concentration from 5 to 100 ng/ml blood sample, more preferably from 10 to 50 ng/ml, especially from 10 to 20 ng/ml, in particular 10 ng/ml.

The histamine release-enhancing effect of histamine cells is conjectured to arise as a result of a triggering effect on cells which are under the influence of a histamine release-inducing agent.

Quite apart from the histamine release-enhancing effect, the deliberate inclusion of a moderate background concentration of histamine is advantageous when employing a detection method such as that employed in a preferred embodiment of a method as disclosed in the invention, namely a fluorometric method, in that raising the base line level of fluorescence due to histamine considerably reduces the uncertainty in the determination of the lowest levels of histamine release from cells.

A further aspect of the invention comprises the use of special washing procedures employing media containing agents promoting the displacement of, or by the degradation of, non-specifically bound blood components, thereby further facilitating the use of whole blood in the analysis.

Such agents may be selected from a group comprising agents influencing surface tension in the media employed, preferably surface active agents (surfactants), notably detergents. The detergent may be an anionic, a cationic, a zwitterionic or a non-ionic detergent, preferably a non-ionic detergent. Examples of suitable detergents are given below.

TABLE 2

Detergents

Anionic Detergents
alkylsulfate salts, such as sodium laurylsulfate, triethanolammonium laurylsulfate, triethanolammonium cetylsulfate and triethanolammonium oleylsulfate, alkylsulfonate salts, such as "Hostapur SAF-60" [the latter being of the type $CH_3CH(R)SO_3^-$, $Na^+$; R = long-chain alkyl] alkylbenzenesulfonate salts, such as sodium dodecylbenzenesulfonate.

Cationic Detergents
quaternary ammonium salts, such as cetyltrimethylammonium bromide and "benzalkonium chloride" [the latter being a mixture of alkyldimethylbenzylammonium chlorides of the general formula $C_6H_5CH_2N(CH_3)_2(R)^+$, $Cl^-$, where R = $C_8-C_{18}$ alkyl].

Zwitterionic Detergents
the "Sulfobetaines", "Lysolecithin", "Empigen BB", "Zwittergent 3-12" and "Zwittergent 3-14"

Non-Ionic Detergents
alkylphenylpolyoxyethylenes, including nonylphenylpolyoxyethylenes such as "Berol 09" and p-tert-octylphenylpolyoxyethylenes such as "Triton X-100", "Triton X-102", "Triton X-114" and "Triton X-165", polyoxyethylene alcohols, such as "Brij 35", "Brij 38", "Lipal 9LA", "Lipocol C-20", "Lauromacrogol 400" and "Cetomacrogol 1000", polyoxyethylene sorbitol esters, such as "Tween 80".

When appropriate, a mixture of different detergents may be employed.

A suitable agent may also be an enzyme which alters the structure of one or more of the interfering components so as to promote their displacement from the histamine-binding material. Such an enzyme may, for example, be a proteolytic enzyme degrading proteinaceous blood components into smaller fragments. Examples of commercially available "broad-spectrum" proteolytic enzymes are: "Alcalase", "Esperase", "Savinase", "Maxatase" and "Rapidase".

In another aspect, a detergent/enzyme combination of agents may be employed. A preferred combination of this type is "Biotrinon" (Bie & Berntsen, Denmark), containing the non-ionic detergent "Berol 09" and the protease "Alcalase" (vide supra). In the method as implemented at the present time it has been found advantageous to include a small quantity of. "Renafix" (a detergent-preparation comprising both non-ionic and anionic detergents), in the detergent/enzyme solution.

Samples subjected to the method of the invention may be biopsy samples. The biopsy material may be any material obtained from a human being or animal, provided that said material comprises cells capable of releasing histamine. The biopsy may be obtained from a tissue part of the respiratory system, in particular tracheobronchial tract, and lung tissue; the gastrointestinal tract; material from peritoneal or pleural cavities; or pathological tissue.

Often biopsy material obtained during an endoscopy procedure is employed, e.g. endoscopy of the gastrointestinal tracts such as the stomach duodenum, and/or jejunum/ileum. Furthermore, cells obtained via bronchoscopy may be examined.

The biopsy material should be kept under suitable conditions, i.e. kept in suitable media. A typical cell dispersion procedure is to cut the biopsy material into minor pieces and subjecting said pieces into medium containing e.g. collagenase, and subsequently incubating so as to obtain a preparation comprising dispersed cells. An example of a his&amine-releasing cell-enriched preparation is a mast cell and/or a basophilic leucocyte preparation.

Further aspects of the invention relate to a method and a test set for identifying or quantitating an agent capable of inducing release of istamine from histamine-containing cells. The method comprises incubating, in a medium, the agent with cells capable of releasing histamine into the medium when contacted with said agent, contacting the medium with a conglomerate which comprises (a) a material which is capable of binding histamine, and (b) a binder, such that at least part of the histamine in the sample is bound to the histamine-binding material;

determining the amount of histamine in the sample on the basis of the amount of histamine bound, correlating said bound histamine amount to standard values obtained for known amounts of the agent; and identifying or quantifying the agent.

Figures 1, 3:
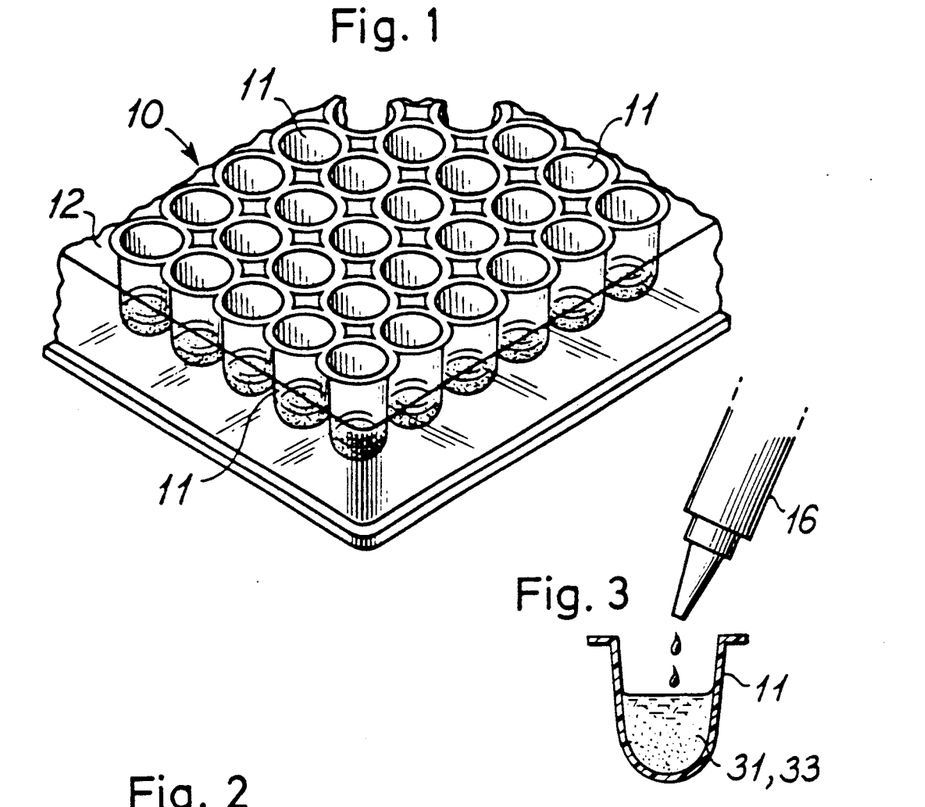

A commercial test set useful for this procedure is a set as illustrated, e.g., in FIG. 1, the wells in this embodiment of the test set being free from allergens.

Standardization procedures employing these aspects of the invention will provide simple a: d reproducible standardization of a wide range of allergens because they are based on what could be designated as a "miniature in vivo allergic reaction".

DETAILED DESCRIPTION OF THE DRAWINGS

FIG. 1 shows, in perspective, a part f a microtiter tray 10 having wells 11 extending downward from an upper surface 12.

Each of the wells 11 contains at its bottom a fixed conglomerate comprising histamine-binding bodies such as will be explained in detail in connection with FIG. 2.

Figure 2:
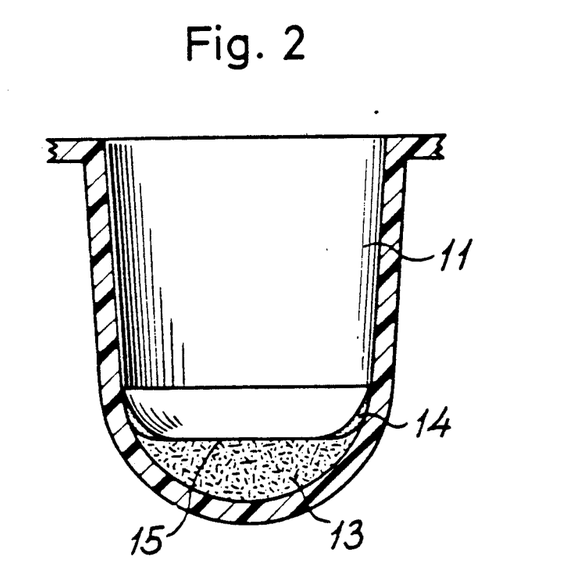
FIG. 2 shows an enlarged sectional view of one of the wells shown in FIG. 1, FIGS. 3-5 show the steps in the process of tray preparation and treatment.

FIG. 2 shows a cross section of one of the wells 11 as shown in FIG. 1. A conglomerate 13 at the bottom of the well consists of bodies of histamine-binding material such as glass microfibers of a length between 2 and 20 m and a thickness of between 0.3 and 2 m bound by means of a binder such as a vinyl acetate/ethylene copolymer, applied from an aqueous suspension thereof. 14 designates a binder meniscus which is often found to be formed above the main part of the conglomerate, and 15 designates the upper surface of the conglomerate. The fibrous conglomerate, the preparation of which is performed e.g. as described in Example 1, has a fiber concentration (or, otherwise expressed: porosity) determined by a number of factors such as the size and the 
size-distribution of the microfibers in the conglomerates and the manner in which the conglomerate has been formed, such as explained and illustrated herein.

Figure 4:
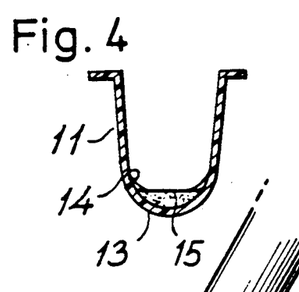

FIGS. 3–4 illustrate steps in the process of preparing the conglomerates at the bottom of the wells 11. In FIG. 3, a suspension comprising glass microfibers and binder such as a dispersed vinylacetate/ethylene copolymer binder as described above and illustrated in Example 1 is applied in a well 11 form a dispenser 16. The suspension is typically an aqueous suspension as described in Example 1. The presence of both the fibers and the dispersed microparticles of the binder is symbolized by the Nos. 31 and 33.

FIG. 4 illustrates the situation after the dispersion applied in FIG. 3 has been allowed to evaporate and to result in a structure corresponding to the one explained in connection with FIG. 2.

Figure 5:
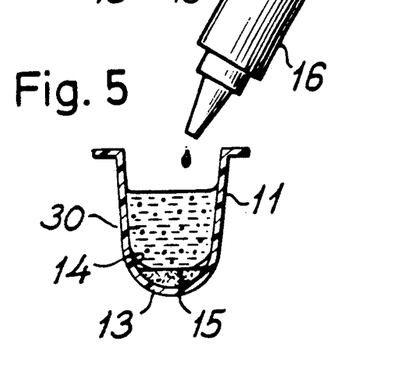

FIG. 5 illustrates an example of the introduction of a liquid distribution 30 (the solution) of a histamine release inducing agent such as an aqueous solution of an allergen in the well. After the introduction of the aqueous solution 30 the water is evaporated so as to leave a well comprising the conglomerate 13 with its upper layer 15 combined with the histamine release-inducing agent. Depending on the chemical character and molecular size of the histamine release-inducing agent it will be combined with the conglomerate. As the histamine-inducing agent is thus applied from a liquid which is evaporated, the manner in which the histamine release-inducing agent such as an allergen would be placed in combination with the conglomerate 13 in the well will depend on various factors such as the chemical character of the allergen, the molecular size of the allergen, etc., but at any rate the histamine release inducing agent should be arranged in such a manner in combination with a conglomerate that the sample will contact the allergen prior to or substantially simultaneously with its contact with the conglomerate. It should be understood, however, that the main feature of this aspect of the invention is not in which exact time wise sequence the sample will contact the conglomerate and the allergen but rather that the allergen thus is present in the wells prior to the introduction of the sample and is capable of inducing histamine release from cells in the sample (depending upon the reaction of the sample to the allergen) in such a manner that an amount of histamine representative of the released histamine becomes bound to the histamine-binding material of the conglomerate and can thus be determined by the method of the invention.

FIG. 6 is discussed in Example 6.1.

FIGS. *7a* and *7b* are discussed in Example 8.

FIG. 8 illustrates another embodiment of a test set useful for the method of the invention and comprising a container with contents (in its entirety designated 17). The container may be a cylindrically shaped container 18 such as a column packed with fixed or confined histamine-binding material. In a container column 18 made of a suitable material, such as polystyrene, a bed or layer 19 of bodies of a histamine-binding material, in particular particles or fibres made of silicon dioxide-based material, especially glass material, is arranged fixed or confined by means of a bottom filter 20 and optionally a top filter 21.

As an alternative, the histamine-binding bodies, especially in the form of particles such as powders, or fibers such as microfibers, especially prepared from glass material, may be present in the form of a conglomerate comprising a binder and said bodies. In a particular embodiment, the layer 19 may designate a layer comprising fibers which in themselves show no, or substantially no, histamine-binding capacity, but which act as a support for particles such as powders or fibers of histamine-binding material distributed in the fibrous mass constituted by the first mentioned fibers which have no or substantially no histamine-binding capacity. In this manner, histamine-binding materials which might in themselves have geometric properties which would not be optimal for the flow of a sample through the layer and/or which would not have a sufficient filter or distributing effect might be useful when combined with the fibers which act as support therefor.

The optional filter 21 at the top of the layer 19 may serve as a further confining boundary for the layer 19, and it may be provided, e.g. at the top thereof, with a material to which a sample of a body fluid or body tissue should be exposed prior to contact of the sample with the histamine-binding material, for example an allergen. In the embodiment shown in FIG. 8, the layer 19, whether consisting of one kind of bodies or a composite of two or more kinds of bodies as explained above may, if desired, also be present in the form of one or more conglomerates, in which a binder conglomerates the particles or fibers present.

It will be understood that the composition explained in connection with the layer 19 may also be useful in the layer 13 arranged in a well as explained and shown in connection with FIG. 2, that is, also such a layer might comprise "inactive fibers" which act as a support and/or distribution material for e.g. bodies of histamine-binding material, the bodies optionally being conglomerated with the fibrous material by means of a binder. If such a composite layer is prepared by sedimentation, the sedimentation rates of particles such as powder particles should be adapted to the sedimentation rate of the fibers so that the desired distribution of the powder in the fibrous masses is obtained, and/or fibers should be sedimented before the powder so that a fibrous layer is first formed whereupon powder and optionally further amounts of fiber are arranged. The result may then either be a substantially homogenous distribution of the histamine-binding bodies in the fibrous mass, or bodies arranged substantially in a layer or layers in the fibrous mass.

The container 17 may confine a volume of several milliliters, and for instance may be a tube with a diameter of several millimeters, or it may be a capillary tube, depending on the particular procedure employed.

EXAMPLE 1

Preparation of glass fiber coated Microtiter trays (batches of 200–400 trays)

a. Preparation of glass fiber suspension

To obtain crushed glass microfibers, Whatman GF/B glass microfiber filter sheet (5 g) was cut into pieces of 2 cm×2 cm and milled in a Retch ball-mill operated in the following manner:

automatic discontinuous mode, i.e. 18 sec run in one direction, 5 sec stop, 18 sec run in the opposite direction, rotation speed 80% of max.

treatment time 5 min

A portion of 24 g of the crushed glass fibers (obtained by a total of 5 runs as above) was suspended in 1000 ml of freshly distilled water in a 1 liter brown glass bottle at ambient temperature.

The suspension was agitated thoroughly for 1 min and then transferred immediately to two 1000 ml glass beakers (500 ml in each; liquid height 8 cm in each beaker).

The crushed fibers were then allowed to sediment for 2 min at ambient temperature, after which the supernatant was transferred to a clean 1 liter brown glass bottle by careful decantation. This supernatant contains crushed fibers of dimensions from ca. 2 m to ca. 20 m.

A 15 ml aliquot of supernatant crushed glass fiber suspension prepared as above (hereafter called crushed glass fiber suspension) was evaporated to dryness in an oven at 95° C. The crushed glass fiber residue weighed 0.33 g, corresponding to a crushed glass fiber content in the suspension of 22 g per liter.

b. Preparation of binder dispersion

For this purpose a commercially available vinyl acetate/ethylene copolymer dispersion (Vinnapas-Dispersion EP 400; Wacker Chemie Danmark A/S, Denmark) was employed. The latter product has a dry matter content of ca. 55% (w/w) and a density of ca. 1.06 g/cm$^3$, the predominant emulsion particle size being ca. 0.8 m (20° C.); Polyvinyl alcohol is incorporated as an emulsion stabilizer.

The latter dispersion was further diluted in freshly distilled water (100 mg EP 400 per ml water) by thorough agitation at ambient temperature.

c. Preparation of binder/crushed glass fiber dispersion 12.5 ml of binder dispersion prepared as above was added to 1000 ml of crushed glass fiber suspension and the mixture was agitated for 2 min.

600 ml of the resulting binder/crushed glass fiber dispersion was transferred to a 1000 ml glass beaker and stirred magnetically for at least 2 min before initiating the tray coating procedure, the stirring being such that gentle movement of the surface of the suspension was visible. Stirring was maintained throughout the dispersion dispensing stage of the tray coating procedure (see below).

d. Coating of Microtiter trays

A 12 channel peristaltic pump (Paxall; fitted with silicone rubber tubing: inner diameter 0.65 mm, outer diameter 2.45 mm, length 60 cm) was used to transfer binder/crushed glass fiber dispersion to the wells of polystyrene Microtiter trays (Nunc, Denmark; 8×12 wells). The pump was operated in the following manner: delivery adjusted to give 50 l per well
  speed: setting 3
  filling volume: setting 2

The pump was activated manually using a foot pedal.

The pumping system was equilibrated after 10 dosages. After filling 5 Microtiter trays, they were immediately placed in a Termaks oven (temperature 95°±2° C.) and dried overnight.

The trays were then removed from the oven and stored in plastic bags until ready for the allergen coating procedure (shelf life: minute 6 months).

EXAMPLE 2

Preincubation with Allergins

EXAMPLE 2.1. Inhalation allergen coating of the glass fiber coated trays (batches of 60 trays)

Trays prepared as described in Example 1 were employed. The following solutions were prepared:
  stock human serum albumin solution: 0.3 mg human serum albumin (SIGMA) per 100 ml distilled water;
  working human serum albumin dilution (HSA): 180 l stock human serum albumin solution was diluted with 100 ml distilled water (this solution was stored in a refrigerator);
  stock histamine solution (100 mg/l): 100 mg histamine made up to 1 liter with distilled water; working histamine solution (WHS) 5 mg/l): 250 l stock solution was diluted to 5 ml with distilled water;

An anti-IgE standard (denoted AIS in the following) purchased from Behringwerke, Germany (400,000 U/ml) was used for the wells containing anti-IgE.

The Microtiter wells are designated as follows: horizontal rows: A–H, vertical columns: 1–12. Each well was filled with 25 l of a solution prepared as outlined below, dispensed from a dosaging apparatus.

| Histamine standards: | |
|---|---|
| Well A1: 50 ng/ml | 210 l WHS + 20790 l HSA = |
| Well B1: 40 ng/ml | 5600 l of solution for A1 + 1400 l HSA = |
| Well C1: 30 ng/ml | 4200 l of soln. for A1 + 2800 l HSA = |
| Well D1: 20 ng/ml | 2800 l of soln. for A1 + 4200 l HSA = |
| Well E1: 10 ng/ml | 1400 l of soln. for A1 + 5600 l HSA = |
| Well F1: 0 ng/ml | 0 l of soln. for A1 + 7000 l HSA = |
| Well G1: 0 ng/ml | 0 l of soln. for A1 + 7000 l HSA = |
| Well H1: 10 ng/ml | 1400 l of soln. for A1 + 5600 l HSA = |
| Well A2: 20 ng/ml | 2800 l of soln. for A1 + 4200 l HSA = |
| Well B2: 30 ng/ml | 4200 l of soln. for A1 + 2800 l HSA = |
| Well C2: 40 ng/ml | 5600 l of soln. for A1 + 1400 l HSA = |
| Well D2: 50 ng/ml | 210 l of soln. for A1 + 20790 l HSA = |
| Anti-IgE standards: | |
| Well E2: | 225 l AIS + 11250 l HSA |
| Well F2: | 600 l of soln. for E2 + 3150 l HSA |
| Well G2: | 112 l of soln. for E2 + 4388 l HSA |
| Well H2: | 112 l of soln. for E2 + 4388 l HSA |
| Well A3: | 112 l of soln. for E2 + 4388 l HSA |

Inhalation allergen standard: Columns 3–12 (with the exception of well A3) (inhalation allergen extracts supplied by Pharmacia, Sweden: 100,000 BU/ml for birch, grass and mugwort, 10,000 BU/ml for all the others).
  Column 3: birch (Betula verrucosa)
  Column 4: grass (Phleum oratense)
  Column 5: mugwort (Ambrosia artemisifolia)
  Column 6: horse dander
  Column 7: dog dander
  Column 8: cat dander
  Column 9: dust mite (Dermatophagoides pteronyssinus)
  Column 10: dust mite (Dermatophagoides farinae)
  Column 11: mould fungus (Alternaria tenuis)
  Column 12: mould fungus (Cladosporium herbarum)
  Row A and Row B (except well A3 in the case of birch):
  for birch, grass and mugwort: 80 l allergen extract + 7920 l HSA;
  for all the other allergens: 800 l allergen extract + 7200 l HSA;
  Row C: 840 l of the soln. for A and B + 2160 l HSA
  Row D: 240 l of the soln. for A and B + 2760 l HSA
  Row E: 101.5 l of the soln. for A and B + 4399 l HSA Row F: 870 l of the soln. for A and B + 2130 l HSA
Row G: 234 l of the soln. for A and B + 2766 l HSA
Row H: 67.5 l of the soln. for A and B + 2932.5 l HSA After filling the wells, the trays were dried overnight in an oven at 50° C.

The trays were then tested as follows: The histamine standards in columns 1 and 2 in each of ten trays from each batch were checked by fluorometry (vide infra), and all the wells of three trays from the same batch were also checked fluorometrically, blood samples taken from three donors having known and well-characterized allergies being used for testing the inhalation allergen standards.

Finally, the trays were packed individually in gas-tight foil in a nitrogen atmosphere and batch-marked. Estimated shelf-life: ca. 6 months.

EXAMPLE 2.2. Food allergen coating of the glass fiber coated trays

Trays prepared as described in Example 1 were employed (batches of 60 trays). Apart from the food allergen extracts, the solutions were as described in Example 2.1.

The Microtiter wells are designated as described in Example 2.1. Each well was filled with 25 l of a solution prepared as outlined below, dispensed from a dosaging apparatus.

Histamine standards: as in Example 2.1.
Anti-IgE standards: as in Example 2.1.
Food allergen standards: Columns 3-12 (with the exception of well A3) [food allergen extracts supplied by ALK, Denmark: 1:100 w/v for chicken egg, 1:20 w/v for all the others].

Column 3: cow milk
Column 4: chicken egg
Column 5: rye flour
Column 6: wheat flour
Column 7: oatmeal
Column 8: pork
Column 9: beef
Column 10: codfish
Column 11: soya bean
Column 12: green pea
Row A and Row B (except well A3 in the case of cow milk):
300 l allergen extract + 2700 l HSA
Row C: 679 l of the soln. for A and B + 1750 l HSA
Row D: 637 l of the soln. for C + 1750 l HSA
Row E: 154 l of the soln. for C + 1750 l HSA
Row F: 154 l of the soln. for D + 1750 l HSA
Row G: 707 l of the soln. for F + 1750 l HSA
Row H: 735 l of the soln. for G + 1750 l HSA The trays were dried, tested, packed and batch-marked as described in Example 2.1.

Analysis of Histamine Release

EXAMPLE 3

Specific allergy in patients was determined in the following way:

a. SOURCE OF SAMPLE MATERIAL

Blood was drawn from each patient by venipuncture and collected in suitable plastic or glass tubes (e.g. "Venoject" tubes) containing a suitable anticoagulant, preferably heparin (as e.g. sodium or potassium heparinate), e.g. 0.5 ml of a 30 U heparin/ml solution so as to obtain 3 U heparin per ml blood when 5 ml blood was collected. Usually 5 ml were collected, however 2.5 ml provided enough sample material for testing for allergy to all the allergens in one tray. For testing for allergy to a single allergen, as little as 1 ml of blood was sufficient.

Blood samples were usually stored at 20°-25° C. (higher temperatures result in too rapid denaturation and deterioration of samples, and too low temperatures lead to precipitation). The samples could normally be sent by ordinary mail and were preferably analysed within 24 hours after sample obtainment, although satisfactory analyses could still be obtained after 48 hours.

b. PREPARING SOLUTIONS AND TRAYS TO BE USED IN THE ANALYSES

Trays prepared as described in Examples 2.1 and 2.2 were employed.

The following solutions were prepared:
working human serum albumin (HSA) dilution: as in Example 2.1;
working histamine solution (WHS) (5 mg/l): as in Example 2.1;
PIPES buffer: 3.02 g PIPES [piperazine-N,N'-bis(2-ethanesulfonic acid)], 19.05 g sodium acetate and 0.49 g potassium acetate, 20-21 ml 1M TRIS [tris(hydroxymethyl)aminomethane] solution (to give final pH 7.4), 600 l 1M CaCl$_2$ and 1100 l 1M MgCl$_2$ are made up to 1 liter with distilled water. This stock solution is kept in a refrigerator;
working buffer: to PIPES buffer was added, immediately prior to use, glucose (1 g per liter PIPES buffer), HSA (1.6 ml per liter PIPES buffer) and heparin solution (LEO, sodium heparinate, 5000 IU per ml; 3 ml per liter PIPES buffer) (the heparin solution was stored in a refrigerator);
intermediate histamine-buffer solution (IHBS) (100 ng/ml) 100 l WHS was diluted to 5 ml with working buffer;
background histamine-buffer solution (HBS) (10 ng/ml): 5 ml intermediate histamine-buffer solution was diluted with 45 ml working buffer;
detergent/enzyme solution: 5 mg "Biotrinon" (Bie & Berntsen, Denmark) was dissolved in 10 ml distilled water containing 25 l "Renafix" (Perfection A/S, Tastrup, Denmark);
OPT solution: 5 mg o-phthaldialdehyde (Fluka) was dissolved in 500 l methanol, and this solution was diluted to 10 ml with 0.05 M NaOH; final pH 12.56.
0.59% perchloric acid; pH 1.16.

25 l HBS were introduced (using an "Easy Dispenser") into each well, i.e. 0.25 ng histamine per well, and the tray and the blood sample were then placed in an oven at 38° C. for ½ hour.

25 l blood were then pipetted (using an Eppendorph pipette) into each well, and the tray was then covered and incubated for 1 hour at 38° C. It was then washed five times with deionized water in an immuno-washer apparatus.

50 l detergent/enzyme solution was pipetted into each well (Volac dispensing equipment), and the tray was then covered and incubated for ½ hour at 38° C.

The tray was then washed five times as described above.

75 l OPT solution were added ("Easy Dispenser") to each well, after which the tray was allowed to stand for 10 min at room temperature.

75 l perchloric acid solution were then introduced ("Easy Dispenser") into each well, and the tray was allowed to stand in the dark for 5 min at room temperature.

The fluorescence intensity in the wells was measured at 455 nm using a Perkin Elmer fluorometer. The histamine concentrations obtained for the patients samples were correlated to the standard histamine curves and the values obtained from the anti-IgE containing wells. The amount of histamine release provoked by the various allergens was calculated, and the amounts divided, e.g., into 4 groups: negative reaction, weak positive reaction, medium positive reaction and strong positive reaction.

Analysis for Allergy to Bee and Wasp Venom Allergen

EXAMPLE 4

Trays prepared as described in Example 1 were employed. For analysis using these allergens, the histamine standards, anti-IgE standards and allergen standards were introduced into the appropriate wells immediately before incubation of the trays at 38° C. for 1 hour (as in Example 3). The following solutions were employed:
  intermediate histamine-buffer solution (IHBS) (100 ng/ml): as in Example 3.
  working buffer: as in Example 3.
  anti-IgE standard (AIS): as in Examples 2.1 and 2.2.

The Microtiter wells are designated as described in Example 2.1. Each well was filled with 25 l of a solution prepared as outlined below, dispensed from a dosaging apparatus.

| Histamine standards: | |
|---|---|
| Wells A1,B1,C1,A2,B2,C2: 5000 l IHBS + working buffer | 5000 l |
| Wells D1,D2: 800 l of soln. for A1-C2 + working buffer | 200 l |
| Wells E1,E2: 600 l of soln. for A1-C2 + working buffer | 400 l |
| Wells F1,F2: 400 l of soln. for A1-C2 + working buffer | 600 l |
| Wells G1,G2: 200 l of soln. for A1-C2 + working buffer | 800 l |
| Wells H1,H2: working buffer | 1000 l |
| Anti-IgE standards: | |
| Wells A3,B3,A4,B4: 61 l AIS + working buffer | 3000 l |
| Wells C3,C4: 425 l of soln. for A3-B4 + working buffer | 1500 l |
| Wells D3,D4: 79 l of soln. for A3-B4 + working buffer | 1500 l |
| Wells E3,E4: 375 l of soln. for D3,D4 + working buffer | 1500 l |
| Wells F3,F4: 69 l of soln. for D3,D4 + working buffer | 1500 l |
| Wells G3,G4: 79 l of soln. for E3,E4 + working buffer | 1500 l |
| Wells H3,H4: 379 l of soln. for G3,G4 + working buffer | 1500 l |

Bee/wasp venom allergen standards: Columns 5 and 6: bee venom allergen; Columns 7 and 8: wasp venom allergen.

The allergenic strength of the supplied extracts Pharmacia, Denmark (100 l/mg)] varied, and the highest dilution concentration (to be used in Wells A and B) for a new batch of allergen extract was therefore established by testing against blood from non-allergic test subjects. As before, 25 l aliquots of solutions prepared as outlined below were added to the appropriate wells; the following data are typical:
  Wells A,B: 5 l allergen extract + 995 l working buffer
  Wells C: 97 l of soln. for A,B + 250 l working buffer
  Wells D: 91 l of soln. for C + 250 l working buffer
  Wells E: 22 l of soln. for C + 250 l working buffer
  Wells F: 22 l of soln. for D + 250 l working buffer
  Wells G: 101 l of soln. for F + 250 l working buffer
  Wells H: 105 l of soln. for G + 250 l working buffer The blood sample and the prepared tray were then incubated at 38° C. for ½ hour, after which 25 l blood were added to each well and the analysis was carried out as described in Example 3.

Effect of Preapplication of Histamine (Histamine Background)

EXAMPLE 5

Whole blood samples from 113 patients referred on the basis of suspected allergy were analyzed consecutively. The first group (Group I) consisted of samples from 56 patients, and the second group (Group II) consisted of the remaining 57 samples (ca. 25% of the patients in each group were subsequently found to exhibit allergy to one or more allergens). The blood samples were then analyzed for histamine release after anti-IgE challenge as described earlier, with (Group II) and without (Group I) the addition of histamine-containing background.

The "diagnostic" cut-off value for the histamine release measured was 10 ng/ml blood, i.e. a sample giving rise to a maximum histamine concentration of less than 10 ng/ml blood was considered to originate from a non-responding patient.

The results obtained were as follows (after correction for added histamine background): The mean allergen-provoked histamine release was 31.7 ng/ml in Group II and 25.4 ng/ml in Group I, corresponding to a 25% increase in histamine release in the former relative to the latter.

The number of non-responders in Group II was 8%, and 32% in Group I, corresponding to a reduction by a factor of 4 in the number of non-responders when employing histamine background in the analysis.

Analysis of Temperature Influence on Histamine Release

EXAMPLE 6.1

In one investigation, blood samples from 17 patients were each divided into 2 aliquots, each of which was analysed essentially as described in Example 3, except that one of each pair of aliquots was preheated for ½ hour at 37° C. prior to establishing the contact with allergens and/or anti-IgE, while the other aliquot was kept at ambient temperature (ca. 20°–23° C.). For 12 of the 17 samples, an increase in histamine release of approximately 20% was observed. The values for the remaining samples were either unchanged or only slightly improved.

EXAMPLE 6.2

A blood sample from a patient exhibiting adequate response to anti-IgE was divided into 4 aliquots. Prior to analysis, the sample aliquots were incubated for ½ hour at 20° C., 37° C., 38° C. and 39° C., respectively. 25 l of each aliquot were then transferred to glass fiber coated Microtiter tray wells (4 trays, prepared as in Example 2.1) containing anti-IgE (incorporated in the trays in the same manner as described in Examples 2.1 and 2.2), and the trays were then incubated for 1 hour at the same temperatures as employed for incubation of the sample aliquots.

Histamine release was determined fluorometrically by comparison with histamine standards also incorporated in the trays (cf. Example 3). The results showed that 38° C. was the optimum temperature, the histamine release obtained at 38° C. being 10% greater than at 37° C.

Figure 6:
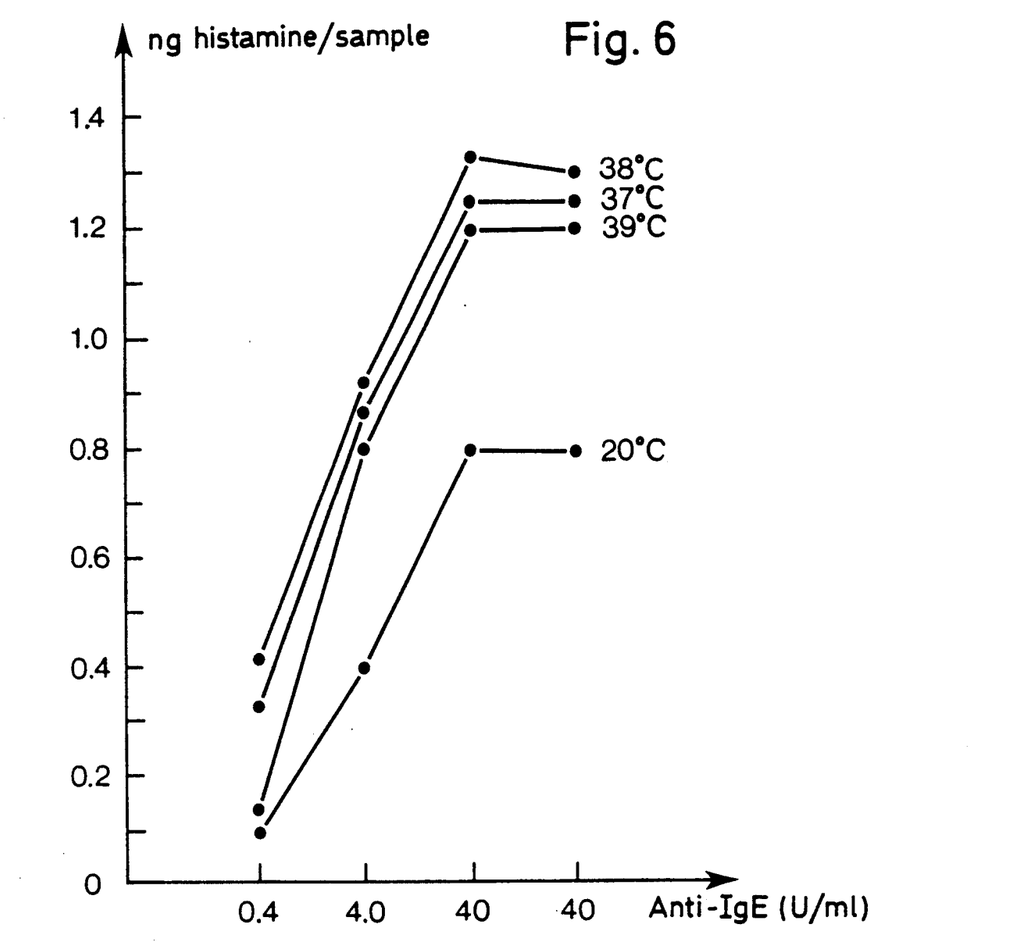
FIG. 6 shows plots illustrating the temperature variation of the amount of histamine released in a whole blood sample (measured in ng histamine per sample) as a function of concentration of anti-IgE; temperatures: 20°, 37°, 38° and 39° C.

The results are shown in FIG. 6.

EXAMPLE 7

To obtain an impression of the effect of the polar polymer with respect to reducing interference with the analysis caused by blood components, the following simple experiment was performed:

192 disks of Whatman GF/B glass fiber filter sheet of diameter 7 mm were stamped out from an intact sheet and introduced into the bottom of the wells of two Microtiter trays of the type shown in FIG. 1 (vide infra). 50 1 of binder dispersion prepared as described in Example 1 were introduced into each well of one of the trays, whereas 50 1 of distilled water were introduced into each well of the other tray. Both trays were then dried as described in Example 1. 25 1 of background histamine buffer and 25 1 of whole blood were then introduced into all the wells of both trays, and the trays were then incubated for 1 hour at 38° C. in an oven, as in Example 3.

The trays were then treated with detergent/enzyme solution and washed with deionized water as described in Example 3, after which it was immediately apparent with the naked eye that the glass fiber disks in the tray without binder retained considerably more blood colour than the glass fiber disks in the other tray, indicating that the ability of at least some haemoglobin-carrying components present in whole blood to bind to the glass fibers in the presence of binder is appreciably reduced relative to the binding ability of the fibers in the absence of binder.

EXAMPLE 8

Preparation of three types of fiber samples for scanning electron microscopy (SEM):

a) A portion of Whatman GF/B glass fiber filter sheet was crushed as described in Example 1. The fibers were deposited onto support suited for SEM;

b) A binder dispersion was prepared as described in Example 1, except that instead of suspension supernatant, the whole mixture of suspended fibers was employed;

c) A Microtiter tray was prepared as described in Example 1, and a section of the microfiber/binder conglomerate was cut out and transferred to a support suited for SEM.

SEM was carried out according to standard procedures, employing a chloroform-based adhesive to affix the material in question to the support, and using Au/Pd-contrast.

Figure 7A:
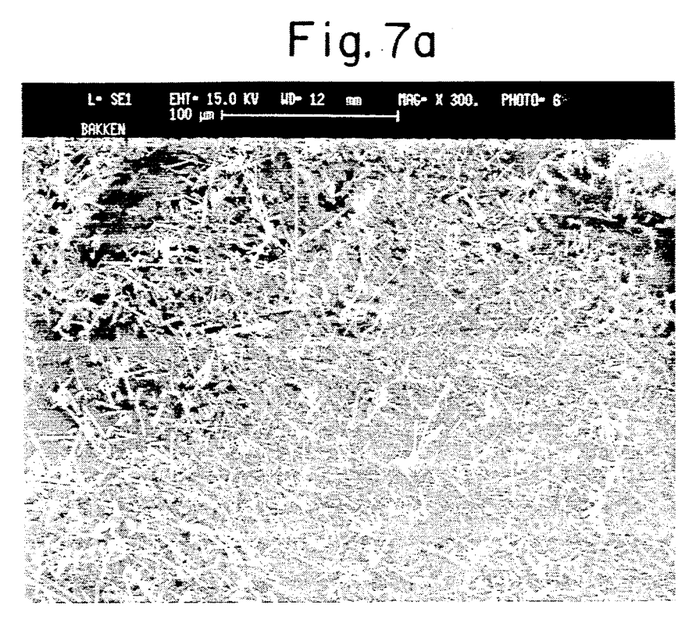
FIGS. 7a and 7b show scanning electron microscopy photographs depicting histamine-binding glass microfibers.
Figure 7B:
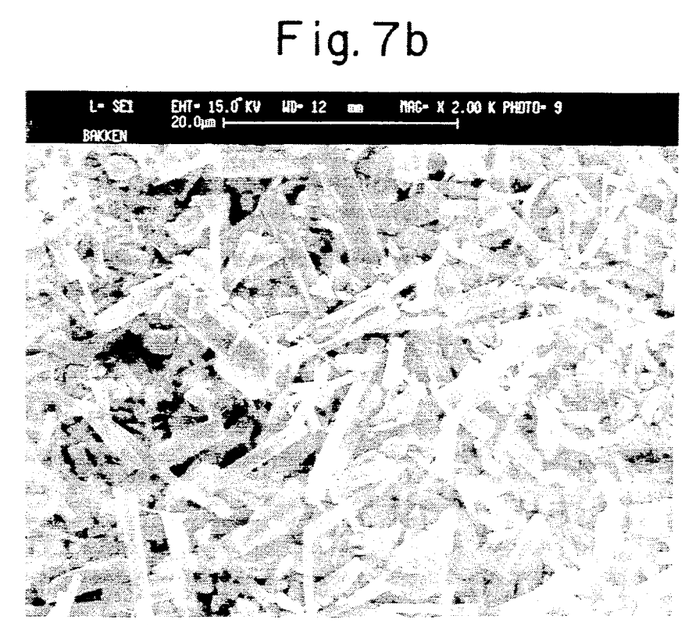
Figure 8:
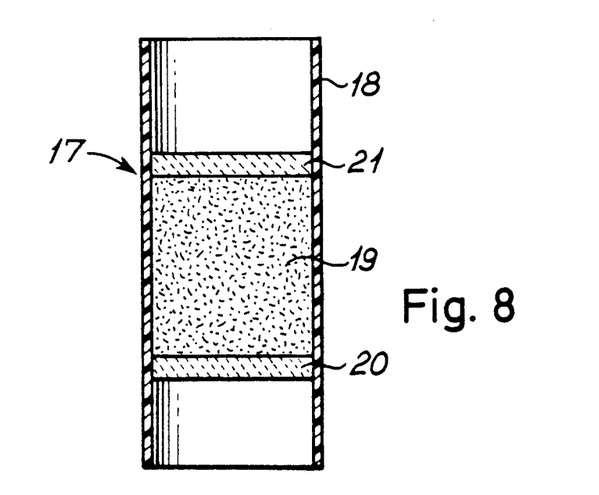
FIG. 8 shows a diagrammatic view of a test set in the form of a column.

FIG. 7a and 7b are photographs of SEM-images at magnifications of 300 ×, and 2000 ×, respectively.

Microfibers of varying dimensions are seen distributed in the fields of vision.

SEM measurement of a representative selection of microfibers was performed, and the following results were obtained:

| length (m) | diameter (m) |
|---|---|
| 14.0 | 0.91 |
| 6.4 | 0.42 |
| 4.5 | 0.53 |
| 4.6 | 0.48 |
| 9.9 | 1.5 |
| 11.3 | 0.9 |

| length (m) | diameter (m) |
|---|---|
| 14.0 | 0.71 |
| 10.2 | 0.92 |

The length:diameter ratios for the fibers were generally from ca. 4 to ca. 15.

We claim:

1. A method for the determination of histamine in a sample which comprises:

contacting the sample with a histamine-binding agent comprising a histamine-binding material which has been treated to reduce the polarity or surface tension of its surface so that its affinity for an interfering component in the sample has been reduced while the histamine-binding capacity of the material has been substantially retained, for a period of time such that at least part of the histamine in the sample is bound to the histamine-binding agent; and determining the amount of histamine in the sample on the basis of the amount of histamine bound.

2. A method according to claim 1 wherein the sample is whole blood or substantially whole blood.

3. A method according to claim 1, wherein the sample is a tissue obtained by biopsy from a human or an animal.

4. A method according to claim 1 wherein the sample is a sample containing hemoglobin or hemoglobin-like components.

5. A method according to claim 1 wherein the histamine-binding agent comprises a histamine-binding inorganic material.

6. A method according to claim 5 wherein the inorganic material is a glass material.

7. A method according to claim 6 wherein the glass material comprises a soda-lime type glass.

8. method according to claim 6, wherein the glass material comprises a borosilicate glass material.

9. A method according to any of claim 1 wherein the treatment of the histamine-binding agent to reduce the polarity or surface tension of its surface has been a treatment with a polar organic polymer.

10. A method according to claim 9 wherein the polar organic polymer comprises a polymer containing heteroatoms such as oxygen or nitrogen atoms.

11. A method for the determination of histamine in a sample which comprises:

contacting the sample with a histamine-binding agent comprising a histamine-binding material which has been treated with a polar organic polymer containing heteroatoms such as oxygen or nitrogen atoms, said polymer selected from the group consisting of polyvinal acetate, a vinyl acetate/ethylene copolymer, and polyvinyl alcohol, said treatment to reduce the polarity or surface tension of its surface so that its afinity for an interfering component in the sample has been reduced while the histamine-binding capacity of the material has been substantially retained, for a period of time such that at least part of the histamine in the sample is bound to the histamine-binding agent; and determining the amount of histamine in the sample on the basis of the amount of histamine.

12. The method of claim 1 wherein the histamine binding agent is a conglomerate of discrete bodies of a histamine-binding material held together by a binder.

13. The method of claim 12 wherein the binder comprises a substance which reduces the polarity of the surface of the histamine-binding material.

14. The method of claim 12 wherein the discrete bodies are glass fibers.

15. A method according to claim 1 wherein the sample is also contacted with an agent capable of inducing histamine release from cells sensitive to the agent, which cells are present in said sample.

16. A method according to claim 15, wherein the histamine release inducing agent is an allergen.

17. A method according to claim 15, wherein the sample is also contacted with an agent capable of enhancing the release of histamine from cells sensitive to the histamine release-inducing agent and present in said sample.

18. A method according to claim 17, wherein the histamine release-enhancing agent is histamine in an amount resulting in a concentration thereof in the sample which is effective to enhance the induced histamine release.

19. A method according to claim 15, wherein the sample is incubated with the histamine release-inducing agent at a temperature of about 37°–40° C.

20. A method according to claim 12, wherein the blood sample is removed after contact with the conglomerate and the conglomerate is washed with a medium comprising an interference-reducing agent which promotes the removal of remaining blood components, said conglomerate remaining intact after washing.

21. A method according to claim 20, wherein the interference-reducing agent is an enzyme.

22. The method of claim 21 wherein the enzyme is a protease.

23. A method according to claim 20 wherein the interference-reducing agent is a detergent.

24. The method of claim 23 wherein the detergent is a non-ionic detergent.

25. A method for the determination of histamine in a sample of whole blood or substantially whole blood, the method comprising:
contacting a whole blood or substantially whole blood sample with a conglomerate which comprises (a) discrete bodies of a histamine-binding material, and (b) a binder which conglomerates such bodies,
permitting at least part of the histamine in the sample to become bound to the histamine-binding material; and
determining the amount of histamine in the sample on the basis of the amount of histamine bound.

26. A method according to claim 1 wherein the histamine-binding material is a glass material.

27. A method according to claim 25 wherein the material is treated to reduce the polarity of or surface tension of the surface of such bodies so that their affinity for an interfering component in the sample has been reduced while the histamine-binding capacity of the inorganic material has been substantially retained.

28. A method according to claim 25 wherein the binder comprises a polar organic polymer.

29. A method according to claim 28 wherein the polar organic polymer comprises a polymer containing heteroatoms such as oxygen or nitrogen atoms.

30. A method according to claim 29 wherein the polar organic polymer is selected from the group consisting of polyvinyl acetate, a vinyl acetate/ethylene copolymer, and polyvinyl alcohol.

31. A method according to claim 30 wherein the polar organic polymer comprises a combination of vinyl acetate/ethylene copolymer and polyvinyl alcohol 32. A method according to claim 11 wherein the polar organic polymer comprises a combination of vinyl acetate/ethylene copolymer and polyvinyl alcohol.

33. A method for identifying or quantitating an agent capable of inducing release of histamine from histamine-containing cells, the method comprising:
incubating, in a medium, the agent with cells capable of releasing histamine into the medium when contacted with said agent,
contacting the medium with an article of manufacture comprising a conglomerate which comprises (a) a plurality of discrete bodies of material which is capable of binding histamine, and (b) a binder conglomerating such bodies,
such that at least part of the histamine in the sample is bound to the histamine-binding material; and
determining the amount of histamine in the sample on the basis of the amount of histamine bound,
correlating said bound histamine amount to standard values obtained for known amounts of the agent; and
identifying or quantifying the agent.

34. A method according to claim 33, wherein the agent is an allergen.

35. The method of claim 27 in which the histamine-binding material's affinity for hemoglobin has been reduced.

* * * * *